(12) United States Patent
Varma

(10) Patent No.: US 6,335,423 B1
(45) Date of Patent: Jan. 1, 2002

(54) BOROXINE COMPOSITIONS

(75) Inventor: Karikath Sukumar Varma, Southport (GB)

(73) Assignee: Pilkington PLC (GB)

( * ) Notice: Subject to any disclaimer, the term of this patent is extended or adjusted under 35 U.S.C. 154(b) by 0 days.

(21) Appl. No.: 09/381,422

(22) PCT Filed: Mar. 19, 1998

(86) PCT No.: PCT/GB98/00838

§ 371 Date: Sep. 20, 1999

§ 102(e) Date: Sep. 20, 1999

(87) PCT Pub. No.: WO98/42802

PCT Pub. Date: Oct. 1, 1998

(30) Foreign Application Priority Data

Mar. 20, 1997 (GB) .................................................. 9705766

(51) Int. Cl.⁷ .................................................. C08G 79/08
(52) U.S. Cl. .......................... 528/394; 528/397; 528/403; 528/421; 528/495

(58) Field of Search ..................................... 528/394, 397, 528/403, 421, 495

(56) References Cited

U.S. PATENT DOCUMENTS 4,450,202 A * 5/1984 Uram et al. ................... 428/412
4,519,926 A * 5/1985 Basalay et al. ................ 252/496

* cited by examiner

*Primary Examiner*—Duc Truong
(74) *Attorney, Agent, or Firm*—Marshall & Melhorn, LLC

(57) ABSTRACT

A boroxine composition having fire and/or flame retardant properties comprising a halo-substituted boroxine in combination with a compound containing an epoxide group curable by the halogenated boroxine compound. A method of making the boroxine comprises reacting the appropriate alcohol with boric acid in the presence of a solvent, usually toluene. In an alternative method, the boroxine is prepared by reacting boric oxide with the corresponding borate, the latter being prepared by reacting the corresponding alcohol with boron trichloride.

16 Claims, No Drawings

BOROXINE COMPOSITIONS

BACKGROUND OF THE INVENTION

1. Field of the Invention

The present invention relates to boroxine compositions and, more particularly, to boroxine compositions which have fire and/or flame retardant properties. The compositions of the present invention are primarily, but not exclusively, intended to be used to cure epoxide or epoxide-type resins.

2. Description of the Related Art

At the present time, amines are generally used to cure epoxy resins. Such compounds do serve the purpose but only react slowly when mixed with the epoxy resin at room temperature. This time period, known as the pot life, is too long for many purposes. Another problem of using amines is that approximately stoichiometric quantities of the amine and epoxide must be used. The amine component of the cured product is highly flammable which is, of course, disadvantageous. Amine-epoxide compositions are not, therefore, suitable for fire-retardant applications unless large amounts of inorganic fillers such as $Al(OH)_3$ or $CaCO_3$ are used. However, these fillers render the composition opaque which makes them of little use in the glass industry.

Boroxines of the general formula:

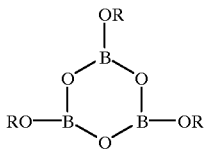

are known. As far as we are aware, the only boroxine which is commercially available is trimethoxy boroxine, that is to say, a compound of the above general formula in which each R represents a methyl group. Other boroxines have been made according to the literature but it appears that they have been made solely as an academic exercise and the literature gives no possible uses for such compounds.

Trimethoxy boroxine, hereafter referred to a TMB, has been used as for curing epoxy resins. The TMB opens the epoxide ring due to the presence of a lone pair of electrons on the oxygen atom of the epoxide group and this attacks one of the boron atoms in the cyclic boroxine structure. This has the advantage over amine-containing curing agents in that the reaction takes place at room temperature. However, there is a concomitant disadvantage which is that an $OR^-$species leading to the production of an alcohol, such as methanol in the case of TMB, is simultaneously produced. Accordingly, a thermosetting resin is produced but highly volatile and inflammable methanol is also produced. This clearly increases the flammability characteristics of the cured material. If the methoxy groups in TMB were to be replaced by higher alkoxy groups, the boiling point of the alcohol produced is increased but the presence of a longer chain in the alcohol group effectively adds to the hydrocarbon content or "fuel" which is present. Accordingly, although the temperature at which the alcohol will ignite is increased, once this temperature is exceeded, the fire will burn more fiercely due to the presence of the additional fuel.

Obviously, if the amount of TMB present in the mixture is increased, the inorganic, that is to say, boroxine content of the mixture also increases. When such material is pyrolysed, it leaves a char which contains some glassy material so that the material is more fire-retardant. More recently, it has been attempted to add a catalyst inhibitor to the trimethoxy boroxine-epoxy resin mixture in an attempt to increase the TMB content so that the fire-retardancy can be increased without affecting the pot life. However to obtain significant improvements in fire retardancy, the levels of TMB needed cannot be attained due to constraints on the use of the inhibitor. One such inhibitor which has been tried is benzyl alcohol used in a ratio of 1 part benzyl alcohol to 3 partsTMB. Whilst this only slightly slows down the rate of curing, the disadvantage is that one is adding to the hydrocarbon content because benzyl alcohol is present as well as the by-product methanol which is produced. The flammability of the mixture is thus increased initially even though the end product of the pyrolysis, the char, contains more glass. It also did not prove possible to get enough TMB units into the polymer produced by the curing to produce a material having adequate heat resistance. In more technical terms, the glass transition temperature was too low as was the heat distortion temperature, this latter being the temperature at which a thermosetting polymer distorts.

When such a system is pyrolysed at approximately 800° C., there is produced, as mentioned above, a charred material or char which contains a glassy material. The charred material also had a thin glassy coating on its exterior. A larger amount than was expected of charred material remained, and this is attributed to the formation of the glassy material. Normally, one would expect a comparatively small amount of charred material to remain because it burns at high temperature to yield carbon dioxide. The smaller than usual loss of charred material has had a greater strength than would normally be expected and this, again was attributed to the formation, in situ, of the glassy material. This is of importance, particularly if the polymeric material is being used as an interlayer between two sheets of glass. It will, of course, be appreciated that if only a small amount of char remains, this effectively means that the carbon has been "lost", that is to say, it has acted as an additional fuel and has been converted into carbon dioxide. Moreover, the loss of carbon will weaken a polymeric structure, particularly if it is being used as a fire-resistant interlayer.

SUMMARY OF THE INVENTION

Although inhibitors do have a beneficial effect insofar as fire retardancy is concerned, they do not provide an ideal solution because they are almost certain to be flammable compounds. Accordingly, we have directed our attention to compounds which, when pyrolysed, produce glass-forming precursors but which have low flammability tendencies and do not necessitate the use of inhibitors.

In our European Patent Specification No. EP 500317A, we disclose a boron compound which does not cure an epoxy resin but does provide a fire resistant composition in combination with the epoxy resin and trimethoxyboroxine as a curing agent therefor. In a preferred aspect of such invention, the boron compound which does not cure the epoxy resin is a boroester derived from a diol and boric acid. When such a compound pyrolises, the organic residues are burnt off and leaves a compound of the formula $B_xO_y$ which is a glass precursor. The alkyl groups, generally methyl groups, do provide flammable components in the mixture. however, this additional flammability is very much less than that caused by the methanol by-product produced during the curing of the epoxy resin.

The present invention therefore seeks to provide a range of fire-retardant compositions which obviates, or at least minimises, the above disadvantages. More particularly, the present invention seeks to provide a range of compositions which have differing reaction times with epoxide groups but which, at the same time, have enhanced fire-retardant properties.

According to the present invention, there is provided a fire-retardant composition comprising a halo-substituted boroxine of the formula:

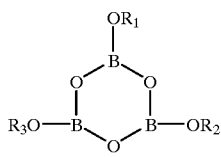

in which $R_1$, $R_2$ and $R_3$, which may be the same or different, each represent a lower alkyl group containing 2 to 5 carbon atoms or an aryl radical, at least one of $R_1$, $R_2$ and $R_3$ being mono- or poly-substituted with at least one halogen substituent, in association with a compound containing an epoxide group which is to be cured, the boroxine being capable of curing the compound containing the epoxide group.

DESCRIPTION OF THE PREFERRED EMBODIMENTS

We have surprisingly found that, by using such boroxine compounds, the fire-retardant properties of the composition are greatly enhanced and that, by varying the length of the alkyl chain and/or by varying the location and number of halogen atoms, we can provide a range of curing compositions having differing pot lives. The reason for this is believed to be that when hydrocarbons per se are pyrolysed, they produce a large number of free radicals which recombine to form mixtures of hydrocarbons which, obviously, are highly flammable. By halogenating the alkyl chain or the aryl group, although the hydrocarbon free radicals are still produced, one or more hydrogen halides are also produced and these both dilute the hydrocarbon free radicals and do not support combustion. In other words, the flammability is substantially reduced. The substitution of organic compounds with halo-substituents is known to have fireproofing effects. However, when the material is, effectively, an organic compound having a substantial inorganic content, it cannot be presumed that the halo-substituents will have such an effect. One reason for this is that halogens normally act as fire-retardant materials in the gaseous phase ultimately producing hydrogen halide species in the gas phase whilst boron tends to act as a fire-retardant in the solid or condensed phase ultimately producing polyborates. There is no evidence in the literature that a combination of these compounds will have an added effect if used in combination, let alone the synergistic effect we have discovered.

Moreover, as will be well known in the art, just because trimethoxyboroxine is effective as a curing agent for epoxy resins, there is no guarantee whatsoever that an halogenated boroxine will cure the resin and, further, there is no indication that the use of such compounds will, in practice, provide improved fire-retardancy.

Another factor which could not be anticipated is that a range of substituted boroxines could produce compositions having a wide range of pot lives. Thus, for example, one can plot the viscosity change when a standard amount of an epoxide is reacted with a standard amount of a boroxine. We have found that if the two boroxines used are n-butoxyboroxine and 4-chlorobutoxyboroxine, the viscosity against time curve for the latter has a gradient which is four times greater than that of the former. This means, in effect, that the pot life of the latter is four times shorter than that of the former.

Thus, we have found that even with carbon chains of four or five atoms, not only do we still obtain a fire-retardant effect but also, even though the halogen atom or atoms are spaced at a considerable distance from the site at which the epoxide attacks the boroxine ring, that the curing rate is increased compared with trimethoxyboroxine itself.

These findings are surprising because one would normally expect that the replacement of an hydrogen atom by a chlorine atom would slow the reaction down due to steric hindrance. One would also expect that electronic inductive effects would also decrease as the substituent is located at a greater distance via several sigma bonds from the boroxine ring.

The alkyl chain may be straight or branched. We have found that branched chain compounds have a shorter pot life than the corresponding straight chain compounds, that is to say, they react faster with the epoxide. This is surprising because one would expect the branched chain compounds to be more sterically hindered than their straight chain counterparts and therefore to react more slowly. The preferred halogens are the fluoride and chloride and the alkyl chain may be mono- or poly-substituted, including perhalo-substituted.

The one or more halogen groups may, if at least one of $R_1$, $R_2$ and $R_3$ is an aryl group, be directly substituted on the aryl moiety or may be provided on an alkyl side chain on the aryl moiety. It is desirable that the halogen is chlorine if it forms a substituent on an alkyl group and that it is fluorine if it forms a substituent on an alkyl or aralkyl group.

The preferred boroxine is selected from the group consisting of tri(2-chloroethoxy)boroxine, tri(2,2-dichloroethoxy)boroxine, tri(2,2,2-trichloroethoxy)boroxine, tri(3-chloro-1-propoxy)boroxine, tri(1,3-dichloro-2-propoxy)boroxine, tri(4-chloro-1-butoxy)boroxine, tri-(3-trifluoromethylbenzyloxy)boroxine, tri(2-fluorobenzyloxy)boroxine, tri(3-fluorobenzyloxy)boroxine, tri(4-fluorobenzyloxy)boroxine, tri(2,3,4,5,6-pentafluorobenzyloxy)boroxine, tri(2,2,3,3-tetrafluorobenzyloxy)boroxine, tri(1H,1H-pentafluoropropoxy)boroxine, tri(1H,1H,5H-octafluoropentoxy)boroxine and tri(1H,1H-heptafluorobutoxy)boroxine.

The preparation of certain boroxines used in the compositions of the present invention will be further described, by way of illustration only, with reference to the following non-limitative Examples:

EXAMPLE 1

3-Chloro-1-propanol (9.45 g:0.1 mol) was added to boric acid (6.18 g:0.1 mol) in toluene (100 ml) and heated in a Dean-Stark apparatus for twenty hours until water (3.6 ml:0.2 mol) had separated out from the reaction mixture. The toluene was removed from the resulting solution by rotary evaporation leaving a clear viscous liquid (12.43 g). Upon analysis, this proved to be tri-(3-chloro-1-propoxy) boroxine. The yield represented 95% of the theoretical yield.

EXAMPLE 2

In a manner analogous to that described in Example 1, tri-(2,2,2-trichloroethoxy) boroxine was prepared from equimolar amounts of boric acid and 2,2,2-trichloroethanol. In this case, the product was a white solid.

EXAMPLE 3

In a manner analogous to that described in Examples 1 and 2, tri-(2-chloroethoxy) boroxine was prepared from equimolar amounts of boric acid and 2-chloroethanol. The product was a viscous liquid containing small rhomboid crystals. The crystals were washed in dry dichloromethane leaving a white crystalline solid. The crystals were washed in dry dichloromethane to leave a white crystalline solid.

EXAMPLE 4

In a manner analogous to the preceding Examples, tri(1,3-dichloro-2-propoxy) boroxine was prepared from 1,3-dichloro-2-propanol and boric acid. These reactants were used in a molar ratio of 1:2 respectively. The toluene was removed by rotary evaporation to leave a clear, colourless, viscous liquid.

EXAMPLE 5

Tri (4-chloro-1-butoxy) boroxine was prepared as in Examples 1 to 4 by reacting equimolar amounts of 4-chloro-1-butanol and boric acid. The toluene was removed by rotary evaporation to leave a clear colourless liquid.

EXAMPLE 6

In a manner analogous to Examples 1 to 5, tri(2,2-dichloroethoxyboroxine) was prepared from 2,2-dichloroethanol and boric acid in a molar ratio of 1:2 respectively. After removal of the toluene by rotary evaporation, a clear light yellow liquid was obtained.

EXAMPLES 7 To 12

In an analogous manner to that described in Examples 1 to 6, tri(3-trifluoromethylbenzyloxy)boroxine, tri(2,3,4,5,6-pentafluorobenzyloxy)boroxine, tri(2-fluorobenzyloxy)boroxine, tri(4-fluorobenzyloxy)boroxine, tri(3-fluorobenzyloxy)boroxine and tri(2,2,3,3-tetrafluoropropoxy)boroxine were prepared by reacting equimolar amounts of boric acid with the appropriate alcohol.

EXAMPLE 13

Tri(1H,1H,2H,2H-perfluorooctoxy)boroxine was prepared by placing $B_2O_3$ (0.28 g:0.004 mol) in a Schlenk tube and heating it under vacuum until the $B_2O_3$ began to melt which was after approximately 5 minutes at 300° C. Tri(1H,1H,2H,2H-perfluorooctyl)borate (4.54 g:0.004 mol) was added to the cooled $B_2O_3$ and stirred at 120° C. for 12 hours until all of the $B_2O_3$ had dissolved. Dichloromethane (50 ml) was then added to the mixture and the resulting solution was filtered to remove impurities. After removal of the solvent, a clear viscous liquid was obtained. The tri(1H,1H,2H,2H-perfluorooctyl) borate was prepared by placing 1H,1H,2H,2H-perfluorooctanol (5.46 g:0.015 mol) in a Schlenk tube with dichloromethane (20 ml) and cooling to 0° C. on an ice bath. $BCl_3$ in dichloromethane (4.5 ml of a 1 M solution:4.5 mmol) was then added slowly to the solution. The reaction mixture was stirred for one hour at 0° C. followed by stirring for four hours at room temperature. The desired product was obtained by removing the solvent under vacuum.

EXAMPLES 14 AND 15

In an analogous way to that described in Example 13, tri(1H,1H,5H-octafluoropentoxy)boroxine and tri(1H,1H-heptafluorobutoxy)boroxine are prepared from the corresponding borate which, in turn is made from the corresponding alcohol.

Two of the above boroxine compounds were subjected to a Limiting Oxygen Test together with trimethoxyboroxine which was used for comparison purposes. The Limiting Oxygen Test (ASTM D2863) is a test well known in the art and is used to find the minimum percentage of oxygen in an oxygen-nitrogen mixture necessary to sustain combustion of a top ignited specimen. The figure obtained is the Limiting Oxygen Index, also known as the Extinction coefficient. The figures which were obtained using a standard resin cured by our two compounds and by trimethoxyboroxine were as follows:

| Compound | Limiting Oxygen Index |
|---|---|
| Trimethoxyboroxine | 19.5 |
| 3-Chloropropoxyboroxine | 20.2 |
| 2-Chloroethoxyboroxine | 20.8 |

As is well documented in the literature, a difference in the Limiting Oxygen Index of the order of 0.1 is regarded as being highly significant.

Moreover, in the above tests, the trimethoxyboroxine sample contained 10% of an organophosphate additive. It is very well known that there is a synergistic effect between organophosphates and halogen-containing organic compounds, particularly with respect to char and flammability. Even if the two halogenated compounds had contained just 5% of an organophosphate additive, which is the minimum amount considered to be of any use, we anticipate the LOI obtained would have been raised to between 21.5 and 22.0.

A check was made to ensure that the halogenated boroxine compounds did, in fact, react with compounds containing epoxide groups. The boroxines tested were trimethoxyboroxine (as a comparison), tri(2-chloroethoxy)boroxine, tri(2,2-dichloroethoxy)boroxine, tri(2,2,2-trichloroethoxy)boroxine, tri(1,3-dichloro-2-propoxy)boroxine, tri(4-chloro-1-butoxy)boroxine, tri(3-chloro-1-propoxy)boroxine, tribenzyloxy boroxine (as a comparison), tri(2,3,4,5,6-pentafluorobenzyloxy)boroxine and tri(3-trifluoromethyl benzyloxy)boroxine. The compounds containing expoxide groups were styrene oxide, trans-stilbene oxide and 1,2-epoxy-3-phenoxy propane.

All of the boroxines reacted with the styrene oxide with the exception of the tri(2,3,4,5,6-pentafluorobenzyloxy) boroxine. This is because the reactions were carried out in the presence of tetrahydrofuran as a solvent and this particular boroxine is insoluble in tetrahydrofuran. The yields of the polymers produced illustrated that all of the boroxines which reacted were efficient epoxide polymerisation initiators and also that, once ring opening has occurred, the reaction goes substantially to completion.

Only tri(3-chlor-1-propoxy)boroxine and tri(4-chloro-1-butoxy)boroxine reacted with the trans-stilbene oxide. This is possibly due to the steric hindrance of the carbocation by the phenyl rings during the propagation stage of the polymerisation. All of the boroxines reacted with the 1,2-epoxy-3-phenoxy propane.

The primary use of the compositions of the present invention is as a curable epoxide-boroxine system. This can, for example, be used as an interlayer sandwiched between two or more sheets of glass or plastics material to provide fireproofing. When heat causes at least one of the sheets of glass or plastics material to fracture or otherwise fail, the fire will attempt to ignite the cured resin. However, as explained hereinbefore, it will not succeed in so doing to any appreciable extent.

What is claimed is:

1. A fire-retardant composition comprising a halo-substituted boroxine of the formula:

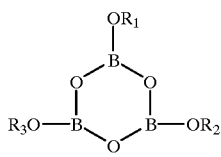

in which $R_1$, $R_2$ and $R_3$, which may be the same or different, each represent a lower alkyl group containing from 2 to 5 carbon atoms or an aryl radical, at least one of $R_1$, $R_2$ and $R_3$ being substituted with at least one halogen atom, and a compound containing an epoxide group which is to be cured, the boroxine being capable of curing the compound containing the epoxide group.

2. A composition as claimed in claim 1 wherein the at least one halo-substituent is chlorine or fluorine.

3. A composition as claimed in claim 1 wherein the at least one alkyl or aryl group is perhalo-substituted.

4. A composition as claimed in claim 1 wherein at least one of $R_1$, $R_2$ and $R_3$ is an alkyl group and the at least one halogen substituent is chlorine.

5. A composition as claimed in any one of claim 1 wherein at least one of $R_1$, $R_2$ and $R_3$ is an aryl or aralkyl group and the at least one halogen substituent is fluorine.

6. A composition as claimed in claim 1 wherein at least one of $R_1$, $R_2$ and $R_3$ is an aryl group and the at least one halogen is directly substituted on the aryl moiety.

7. A composition as claimed in claim 1 wherein at least one of $R1$, $R_2$ and $R_3$ is an aryl group having at least one alkyl chain substituent substituted with the at least one halogen atom.

8. A composition as claimed in claim 1 wherein the boroxine is selected from the group consisting of tri(2-chloroethoxy)boroxine, tri(2,2-dichloroethoxy)boroxine, tri(2,2,2-trichloroethoxy)boroxine, tri(3-chloro-1-propoxy)boroxine, tri(1,3-dichloro-2-propoxy)boroxine, tri(4-chloro-1-butoxy)boroxine, tri(3-trifluoromethylbenzyloxy)boroxine, tri(2-fluorobenzyloxy)boroxine, tri(3-fluorobenzyloxy)boroxine, tri(4-fluorobenzyloxy)boroxine, tri(2,3,4,5,6-pentafluorobenzyloxy)boroxine, tri(2,2,3,3-tetrafluoropropoxy)boroxine, tri(1H,1H-pentafluoropropoxy)boroxine, tri(1H,1H,5H-octtafluoropentoxy)boroxine and tri(1H,1H-heptafluorobutoxy)boroxine.

9. A method of making a composition as claimed in claim 1 comprising reacting boric acid with the corresponding alcohol in the presence of a solvent, removing the solvent and adding the boroxine compound thus produced to the compound containing the epoxide group to be cured.

10. A method as claimed in claim 9 wherein the solvent is toluene.

11. A method of making a composition as claimed in claim 1 comprising the steps of reacting boric acid with the corresponding borate in the presence of a solvent and adding the boroxine thus produced to the compound containing the epoxide group to be cured.

12. A method as claimed in claim 11 wherein the solvent is dichloromethane.

13. A method as claimed in claim 11 wherein the borate is prepared by reacting the appropriate alcohol with boric trichloride in the presence of a solvent.

14. A method as claimed in claim 13 wherein the solvent is dichloromethane.

15. A thermosetting curable fire-retardant epoxy composition comprising a halo-substituted boroxine of the formula:

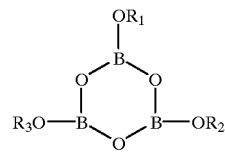

in which $R_1$, $R_2$ and $R_3$, which may be the same or different, each represent a lower alkyl group containing from 2 to 5 carbon atoms or an aryl radical, at least one of $R_1$, $R_2$ and $R_3$ being substituted with at least one halogen atom, and a compound containing an epoxide group which is to be cured, the boroxine being capable of curing the compound containing the epoxide group.

16. A fire proof glazing which comprises an interlayer sandwiched between two or more sheets of glass or plastic material wherein the interlayer has been produced by the method of claim 9.

* * * * *